United States Patent
Jasinski

(10) Patent No.: US 7,819,034 B2
(45) Date of Patent: Oct. 26, 2010

(54) REDUCTION OF WIRE NUMBERS IN A PAPER SCANNER POWER TRACK

(75) Inventor: Wojtek T. Jasinski, Burnaby (CA)

(73) Assignee: Honeywell ASCa Inc., Mississauga (CA)

( * ) Notice: Subject to any disclaimer, the term of this patent is extended or adjusted under 35 U.S.C. 154(b) by 536 days.

(21) Appl. No.: 11/973,942

(22) Filed: Oct. 10, 2007

(65) Prior Publication Data

US 2009/0099682 A1    Apr. 16, 2009

(51) Int. Cl.
G01N 33/24    (2006.01)
G01D 11/00    (2006.01)

(52) U.S. Cl. .......................... 73/866.5; 73/159
(58) Field of Classification Search ............... 73/866.5, 73/159
See application file for complete search history.

(56) References Cited

U.S. PATENT DOCUMENTS

| | | | |
|---|---|---|---|
| 4,071,911 A | 1/1978 | Mazur | |
| 4,767,935 A | 8/1988 | Anderson et al. | |
| 4,786,817 A | 11/1988 | Boissevain | |
| 4,879,471 A | 11/1989 | Dahlquist | |
| 4,982,334 A | 1/1991 | Balakrishnan | |
| 5,022,966 A | 6/1991 | Hu | |
| 5,081,586 A | 1/1992 | Barthel et al. | |
| 5,166,748 A | 11/1992 | Dahlquist | |
| 5,539,634 A | 7/1996 | He | |
| 5,737,190 A | 4/1998 | Marshall et al. | |
| 5,773,714 A | 6/1998 | Shead | |
| 5,853,543 A | 12/1998 | Hu et al. | |
| 5,892,679 A | 4/1999 | He | |
| 6,059,931 A | 5/2000 | Hu et al. | |
| 6,080,278 A | 6/2000 | Heaven et al. | |
| 6,092,003 A | 7/2000 | Hagart-Alexander et al. | |
| 6,149,770 A | 11/2000 | Hu et al. | |
| 6,281,679 B1 | 8/2001 | King et al. | |
| 6,866,367 B2 | 3/2005 | Szumla | |
| 6,967,726 B2 | 11/2005 | King et al. | |
| 7,023,217 B1 | 4/2006 | Wong | |
| 7,196,771 B2 | 3/2007 | Berger | |
| 7,235,890 B1 | 6/2007 | Jasinski | |
| 2005/0088316 A1 | 4/2005 | Mallison et al. | |
| 2006/0109519 A1 | 5/2006 | Beselt et al. | |
| 2006/0237156 A1 | 10/2006 | Shakespeare et al. | |
| 2006/0255300 A1 | 11/2006 | Shakespeare | |
| 2007/0115509 A1 * | 5/2007 | Shinohara | 358/3.26 |

* cited by examiner

Primary Examiner—Thomas P Noland
(74) Attorney, Agent, or Firm—Cascio Schmoyer & Zervas

(57) ABSTRACT

The performance of scanning systems can be significantly enhanced by replacing the traditional power track with preferably just two wires or transmission channels for effecting communication between (i) the sensors on the mobile carriage of the scanning system and (ii) the controls, power sources, and related devices that are typically located in a compartment or module which is a significant distance away. This can be implemented by employing selected multiplexer and complementary de-multiplexer combinations in the scanner head and in the module. This technique reduces EMI noise, power loss, drag on the moving scanner heads carrying the sensors, and cost of construction.

20 Claims, 2 Drawing Sheets

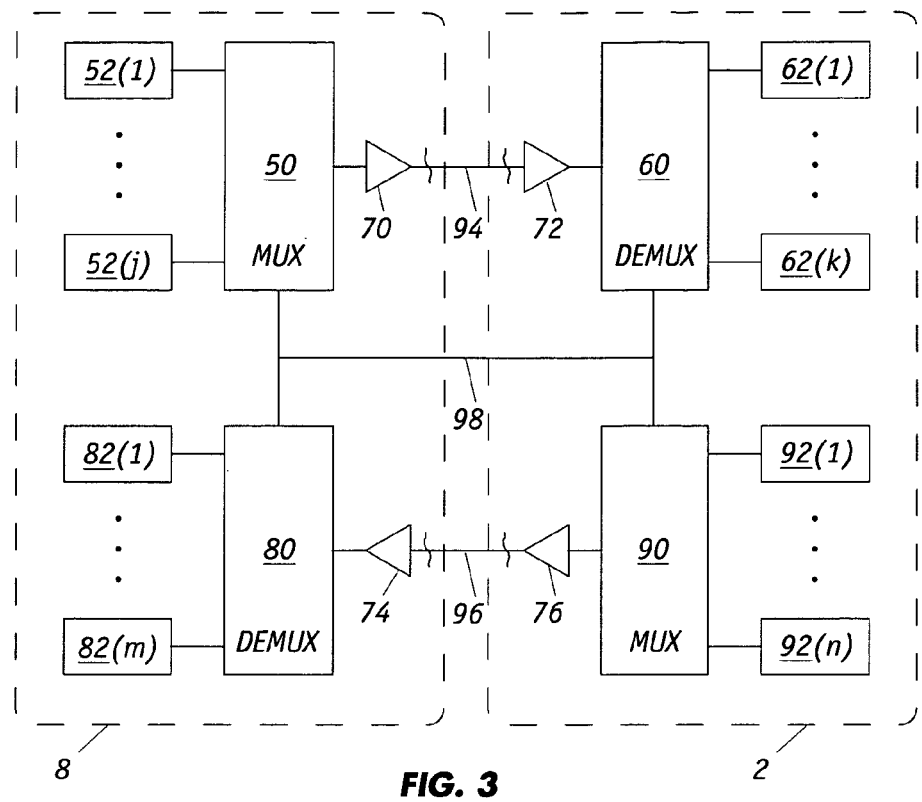
FIG. 3
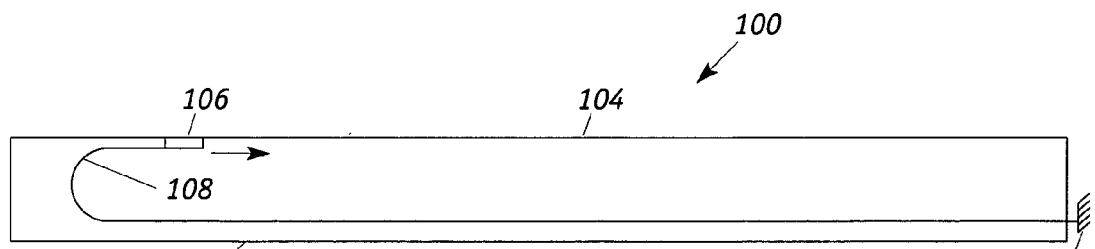
FIG. 4A *(Prior Art)*
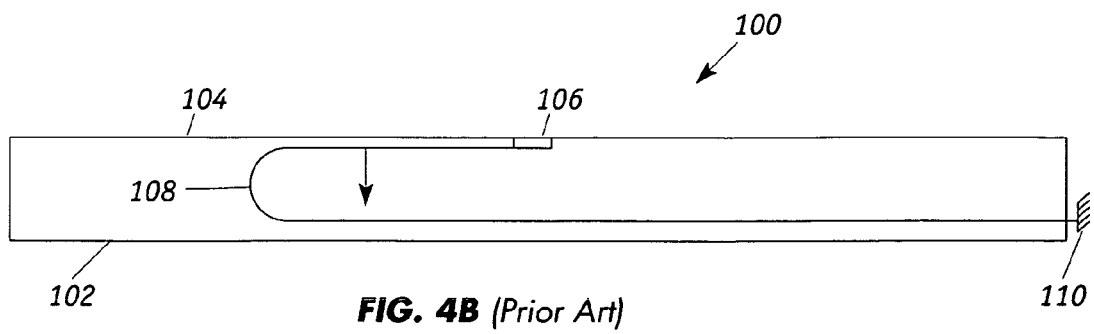
FIG. 4B *(Prior Art)*

REDUCTION OF WIRE NUMBERS IN A PAPER SCANNER POWER TRACK

FIELD OF THE INVENTION

The invention relates generally to a scanning or moving system that is equipped with multiple sensors or other electronic devices requiring a large number of control and measurement wires and more particularly to a technique that reduces the number of wire interconnections linking the sensors to control devices that are located remotely from the moving sensors, which improves system reliability, efficiency and sensitivity and which reduces costs.

BACKGROUND OF THE INVENTION

It is often desirable to obtain measurements of selected characteristics of sheet materials during manufacture. Although various properties of sheet materials can be detected by off-line laboratory testing, such tests often are not practical because of the time required for sample acquisition and analysis. Also, laboratory testing has the shortcoming that samples obtained for testing may not accurately represent sheet material that has been produced.

To overcome the drawbacks of laboratory testing of sheet materials, various sensor systems have been used for detecting sheet properties "on-line," i.e., on a sheet-making machine while it is operating. Typically, on-line sensor devices are operated to periodically traverse, or "scan," traveling webs of sheet material during manufacture. Scanning usually is done in the cross direction, i.e., in the direction perpendicular to the direction of sheet travel. Depending upon the sheet-making operation, cross-directional distances can range up to about ten meters or more.

A wide variety of scanning sensor devices has been developed for on-line measurements of sheet materials. As illustrated in FIGS. 4A and 4B, the scanning sensor system 100 typically includes a stationary frame 102, having a pair of upright end members that stand on a factory floor for supporting a guide member 104 that extends horizontally across a traveling sheet (not shown). A motor driven carriage is mounted to travel on the guide member 104. The carriage is connected to a drive system to be driven back and forth across sheet. The scanning sensor system also includes a scanning head 106 that is mounted on the carriage member. The scanning head 106 contains the detection components. For example, in the case of a spectrometric analyzer, the scanner head can include a source of infrared light, collimating and beam-splitting mirrors, and photosensitive detector.

The scanner head 106 is electronically connected by a large number of wires 108 that are connected to the process controller 110. The scanner head 106 travels back and forth along the cross direction adjacent the traveling sheet being analyzed. In FIG. 4A, the scanner head 106 is at one side of the frame 102 and is moving toward the middle of the frame 102 as shown in FIG. 4B. Wires 108 typically comprise a power chain or track that has either relatively flat or cylindrical, elongated structure that consists of a series of long, parallel conductors that are separated from one another by an insulating material. As the carriage moves back and forth, the wires are subject to fatigue as it undergoes cyclic motion, as well as by abrasion, impact or tension overload. In addition, the weight of the power chain causes the suspended wires 108 to sag because of the lack of adequate support. Consequently, the detection components, that are located in the scanner head, are subject to excessive vibrations. Moreover, the presence of the relatively heavy power chain makes it more difficult to drive the carriage and to control its speed. These phenomena combined reduce the reliability, efficiency and sensitivity of the detectors. The numerous wires in power chains are also subject to electromagnetic interference (EMI) and power losses. The art is in need of techniques for improving the operations of scanning systems by minimizing or eliminating the problems associated with power chains.

SUMMARY OF THE INVENTION

The present invention is based in part on the recognition that the reliability and performance of scanning systems can be significantly enhanced by replacing the traditional power track with preferably just two wires or transmission channels for effecting communication between (i) the sensors on the mobile carriage of the scanning system and (ii) the controls, power sources, and related devices that are typically located in a compartment or module which is a significant distance away. The signal update is in "real time," enabling proper system operation.

In one aspect, the invention is directed to a scanning system, for moving a first set of sensor electronic devices between a first end and a second end along a main scanning direction, which includes:

a mobile carriage, onto which the first set of sensor electronic devices is secured wherein, for at least a plurality of the sensor electronic devices, each has a sensor input;

a first set of control electronic devices that is located remotely from the mobile carriage, wherein for at least a plurality of the control electronic devices, each has a control output;

a control multiplexer that is coupled to the plurality of control electronic devices and that receives input signals therefrom and that provides control signals for transmission through a first transmission channel;

a sensor de-multiplexer that is coupled to the plurality of sensor electronic devices and that receives the control signals from the first transmission channel and that provides sensor signals to selected sensor electronic devices to which the sensor de-multiplexer is coupled; and means for driving a mobile carriage along the main scanning direction.

In another aspect, the invention is directed to an on-line scanning sensor system capable of detecting multiple characteristics of a traveling sheet of paper product as it progresses through or exits from a papermaking machine that includes:

(a) a support member spanning across the traveling sheet of paper product;

(b) a mobile carriage, that is slidably attached to the support member, onto which a first set of sensor electronic devices is secured wherein, for at least a plurality of the sensor electronic devices, each has a sensor input;

(c) a first set of control electronic devices that is located remotely from the mobile carriage, wherein for at least a plurality of the control electronic devices, each has a control output;

(d) a control multiplexer that is coupled to the plurality of control electronic devices and that receives input signals therefrom and that provides control signals for transmission through a first transmission channel;

(e) a sensor de-multiplexer that is coupled to the plurality of sensor electronic devices and that receives the control signals from the first transmission channel and that provides sensor signals to selected sensor electronic devices to which the sensor de-multiplexer is coupled; and (f) means for driving a mobile carriage between a first end and a second end along a main scanning direction such that the mobile carriage scans back and forth across at least a substantial portion of the paper product along a cross direction of the moving sheet, characterized in that the first set of sensor electronic devices is operated to detect a plurality of physical characteristics of the paper product.

In a further aspect, the invention is directed to a method for transmitting signals between sensor electronic devices and control electronic devices that include the steps of:

securing a first set of sensor electronic devices to the mobile carriage wherein, for at least a plurality of the sensor electronic devices, each has a sensor input;

providing a first set of control electronic devices that is located remotely from the mobile carriage, wherein for at least a plurality of the control electronic devices, each has a control output;

providing a control multiplexer that is coupled to the plurality of control electronic devices and that receives input signals therefrom and that provides control signals for transmission through a first transmission channel;

providing a sensor de-multiplexer that is coupled to the plurality of sensor electronic devices and that receives the control signals from the first transmission channel and that provides sensor signals to selected sensor electronic devices to which the sensor de-multiplexer is coupled;

moving the mobile carriage between a first end and a second end along a main scanning direction; and operating the first set of sensor electronic devices and the first set of control electronic devices.

In preferred embodiments, the control multiplexer generates compressed signals through a transmission channel to the complementary sensor de-multiplexer and similarly the sensor multiplexer generates compressed signals through a transmission channel to the complementary control multiplexer. Each de-multiplexer decompresses the signals and provides output updates in "real time" which enables operation of the scanning system.

BRIEF DESCRIPTION OF THE DRAWINGS

FIG. 3 is a schematic diagram of the sensor head and control module illustrating the multiplexer and de-multiplexer devices therein; and FIGS. 4A and 4B illustrate a prior art scanning apparatus.

DETAILED DESCRIPTION OF THE PREFERRED EMBODIMENTS

Figure 1:
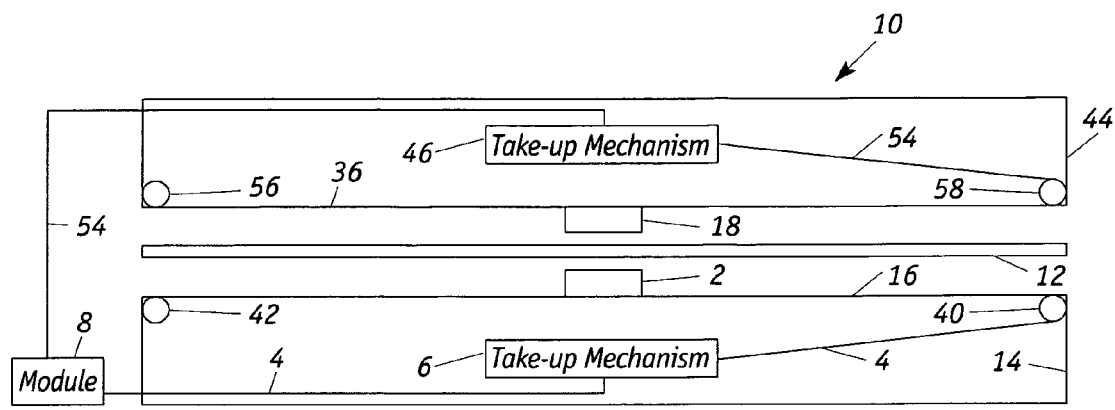
FIG. 1 is a scanning system with mobile carriage sensors connected thereto.

FIG. 1 illustrates an embodiment of the scanning system 10 of the present invention which includes a frame 14 that is constructed of steel or other material of sufficient structural strength. Typically, for scanning systems that are employed to scan in the cross direction of a moving sheet or web 12, such as paper in a papermaking machine, the length of support member 16 of frame 14 is about the same as the width of the moving sheet 12 so that the scanner head 2 is able to traverse the entire width along the cross direction between pulleys 40 and 42. This distance can be six to eight meters or more. In this arrangement, scanner head 2 is positioned underneath sheet 12 to be analyzed, however, it is understood that when only one scanner head is employed, it can be positioned directly above or, at an angle relative to the sheet in order to measure properties from the sheet surface facing the scanner head.

Scanner head 2, which is broadly defined as a light weight structure housing one or more electronic and/or optical devices, is in communication with controls, database and other devices, which are housed in process control compartment or module 8, via transmission channels 4. The present invention is particularly suited for scanner heads that include multiple sensors and electronic components that constitute many data sources that must be connected to control devices kept safely away from the harsh environment of the papermaking machine. As will be described further herein, a feature of the invention is that the number of wires required in the transmission channels 4 is significantly less than that required in prior art scanning systems thereby reducing the weight of the transmission channels.

Preferably the scanning system 10 includes a wire take-up mechanism 6 which routs the moving transmission channels 4 through a path that is defined by pulleys and springs to minimize wear as the scanning head 2 travels back and forth. Suitable up-take mechanisms are described in US Patent Application 2006/0109519 to Beselt et al., which is incorporated herein by reference.

In another embodiment, scanning systems are configured to measure radiation that is transmitted through the sheet. In this arrangement, the sensor comprises two components, a light source and a detector, which are positioned on opposite sides of the moving sheet. As illustrated in FIG. 1, in a dual scanner head arrangement, scanner head 2 can include a detector that monitors radiation that is transmitted through sheet 12 that is illuminated by a beam of radiation from a source located on scanner head 18 which is secured to support member 36 of frame 44. Sensor head 18 is in communication with controls, database and other devices, which are housed in process control module 8, via transmission channels 54. Movement of scanner head 18 between pulleys 56 and 58 is facilitated by take-up mechanism 46.

The movements of the dual scanner heads 2, 18 are typically synchronized with respect to speed and direction so that they are aligned with each other. Scanning systems having sensor components on opposite sides of the sheet being analyzed are described, for example, in U.S. Pat. No. 5,773,714 to Shead and U.S. Pat. No. 5,166,748 to Dahlquist, which are incorporated herein by reference. It is understood however that the top scanner head 18 and bottom scanner head 2 can be designed to move independently of each other as the sensors attached thereon perform measurements of sheet 12. For instance, each scanner head can feature sensors that measure radiation that is reflected from the sheet surface so that the top and bottom scanner heads can function independently.

Figure 2:
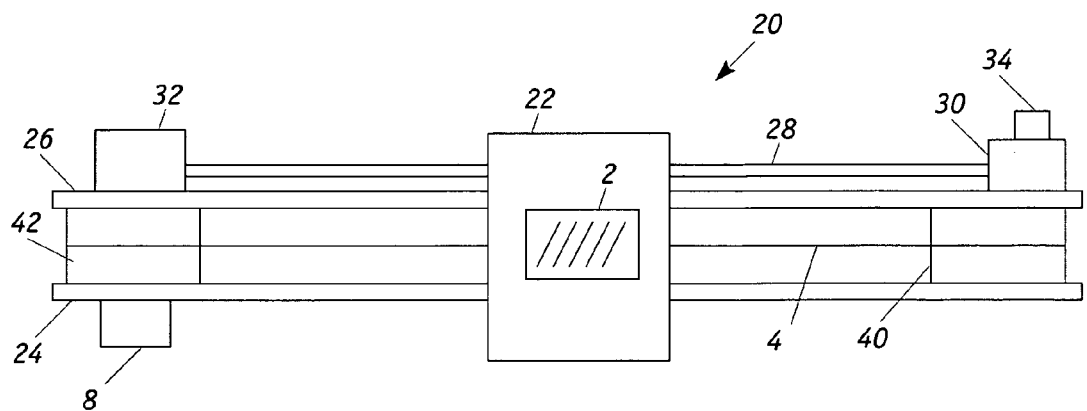
FIG. 2 is a top plan view of the scanning system.

The scanner head 2 can be advanced back and forth along the cross direction by a number of transport mechanisms. In the embodiment illustrated in FIG. 2, the scanning system 20 includes a mobile carriage 22 which is slidably attached to rails 24 and 26 which function as low-friction guides for carriage 22 as it travels or slides back and forth. Carriage 22, which can be a platform with rollers, supports scanner head 2 which is in communication with module 8 via transmission lines 4 which is routed by guide pulleys 40 and 42. Carriage 22 is connected to a belt 28 that is wound around drive pulley 32 and driven pulley 30, which is operatively connected to motor 34. In operation, control of motor 34 regulates the speed and direction of the movement of the carriage 22 which can travel at the speed of 1 to 5 meters per second or higher. Where the scanning system includes two scanner heads, the second head is similarly maneuvered on a mobile carriage and associated mechanism as shown in FIG. 2.

FIG. 3 illustrates the data link between sensor head 2 and process control module 8. Electronic devices which are housed in the mobile sensor head 2 may be generally referred to as "sensor electronic devices" whereas electronic devices which are safely stored in the stationary process control module 8 may be generally referred to as "control electronic devices." It is understood however that the terms are to differentiate the locations of the devices and not to limit their functions. In this example, the control compartment 8 includes output control devices 52(1) through 52(j), which represent any suitable electronic device with output signals, and input control devices 82(1) through 82(m), which represent any suitable electronic device that receives input signals. Similarly, sensor head 2 includes input sensor device 62(1) through 62(k), which represent any suitable electronic device that receives input signals, and output sensor device 92(1) through 92(n), which represent any suitable electronic device with output signals. Each of j, k, m, and n preferably ranges from 2 to 100 or more. Typically, j is equal to k and m is equal to n.

Each input control device 52(1) through 520(j) is connected to an amplifier assembly 70 through a multiplexer 50 which samples and compresses all of the input control devices and transmits the compressed signals through a communication channel 94. Signals from the output control devices are inputs to the multiplexer. At the receiving end of the communication data link, a complementary de-multiplexer 60 decompresses the data stream, which is amplified by amplifier assembly 72, back down into the original streams. The de-multiplexer 60 selects one of the input sensor devices 62(k) and connects the single input to the selected output line. Output signals from the demultiplexer are input signals to the input sensor devices.

Similarly, each output sensor device 92(1) through 92(n) is connected to an amplifier assembly 76 through a multiplexer 90 which samples and compresses all of the output sensor devices and transmits the compressed signals through a communication channel 96. Signals from the output sensor devices are inputs to the multiplexer. At the receiving end of the communication data link, a complementary de-multiplexer 80 decompresses the data stream, which is amplified by amplifier assembly 74, back down into the original streams. The de-multiplexer 80 selects one of the input control devices 82(m) and connects the single input to the selected output line. Output signals from the demultiplexer are input signals to the input control devices.

Conventional high speed multiplexing and de-multiplexing techniques such as time division and frequency division multiplexing can be employed to achieve very fast "real time" communication along with bit compression and decompression techniques.

As is apparent, in this example, only two wires are needed to effect electronics communication between multiple numbers of sensor devices and corresponding control devices. The invention can be readily implemented, for instance, by connecting multiplexer 50 and de-multiplexer 80 of module 8 to a first electronic circuit board and connecting de-multiplexer 60 and multiplexer 80 of sensor head 2 onto a second electronic circuit board. The two electronic circuit boards are interconnected by three communication wires, namely, the two transmission channels 94, 96 and, optionally, a ground wire 98. Even when sensor head 2 and module 8 are separated by a distance of 50 to 100 meters or more, this arrangement provides real time signal updates and the signal update latency can be less than one microsecond. In addition, because the electronic circuit boards provide current locally, the wires do not have to carry large currents over long distance which minimizes power loss and EMI noise is reduced substantially.

As noted above, the scanning system can employ two scanning heads that are attached to separate mobile carriages with each scanner head incorporating appropriate sensor devices. For example, a top scanner head can include multiplexer 90 and the associated electronic devices while a bottom scanner head can include de-multiplexer 60 and the associated electronic devices as illustrated in FIG. 3. In this case, an optional grounding wire can be used with each scanner head. In an embodiment of a more complex design, the scanner system has two scanning heads each with the circuitry shown in FIG. 3.

The scanning system can be employed to measure a variety of web or sheet properties such as fibrous sheets of paper in a papermaking machine, however, it is understood that the scanning system can be employed to measure properties of other materials, including, for example, plastics. In the art of making paper with modern high-speed machines, sheet properties must be continually monitored and controlled. The sheet variables that are most often measured include basis weight, moisture content, fiber orientation, temperature, and caliper, i.e., thickness, of the sheets at various stages in the manufacturing process. Papermaking devices are well known in the art and are described, for example, in U.S. Pat. No. 5,539,634 to He, U.S. Pat. No. 5,022,966 to Hu, U.S. Pat. No. 4,982,334 to Balakrishnan, U.S. Pat. No. 4,786,817 to Boissevain et al., and U.S. Pat. No. 4,767,935 to Anderson et al. which are incorporated herein by reference.

As is apparent, the choice of sensor devices in the scanner head and corresponding control devices in the control module of FIG. 3 depends on the physical characteristics of the paper being monitored and/or the process control being implemented. Sensor devices to measure various properties of paper are described, for example, in US Patent Application 20060255300 to Shakespeare and US Patent Application 20060237156 to Shakespeare et al, U.S. Pat. Nos. 6,967,726 and 6,281,679 both to King et al., which are incorporated herein by reference. Process control techniques for papermaking machines are further described, for instance, in U.S. Pat. No. 6,149,770 to Hu et al., U.S. Pat. No. 6,092,003 to Hagart-Alexander et al, U.S. Pat. No. 6,080,278 to Heaven et al., U.S. Pat. No. 6,059,931 to Hu et al., U.S. Pat. No. 5,853,543 to Hu et al., and U.S. Pat. No. 5,892,679 to He, which are all incorporated herein by reference.

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. A scanning system, for moving a first set of sensor electronic devices between a first end and a second end along a main scanning direction, which comprises:

a mobile carriage, onto which the first set of sensor electronic devices is secured wherein, for at least a plurality of the sensor electronic devices, each has a sensor input;

a first set of control electronic devices that is located remotely from the mobile carriage and which is separated by a distance of at least 50 meters from the mobile carriage, wherein for at least a plurality of the control electronic devices, each has a control output;
a control multiplexer that is coupled to the plurality of control electronic devices and that receives input signals therefrom and that provides control signals of the plurality of control electronics for transmission through a first transmission channel that comprises a first wire;
a sensor de-multiplexer that is coupled to the plurality of sensor electronic devices and that receives the control signals from the first transmission channel and that provides sensor signals to selected sensor electronic devices to which the sensor de-multiplexer is coupled;
a first ground wire that connects the control multiplexer and the sensor de-multiplexer; and
means for driving a mobile carriage along the main scanning direction which has a distance of at least six meters.

2. The scanning system of claim 1 further comprising:
a second set of sensor electronic devices, that is secured to a mobile carriage, wherein for at least a plurality of these sensor electronic devices, each has a sensor output;
a second set of control electronic devices, that is located remotely from any mobile carriage and which is separated by a distance of at least 50 meters from any mobile carriage, wherein for at least a plurality of these control electronic devices, each has a control input;
a sensor multiplexer that is coupled to the plurality of sensor electronic devices of the second set and that receives input signals therefrom and that provides sensor signals of the plurality of sensor electronic devices of the second set for transmission through a second transmission channel that comprises a second wire;
a control de-multiplexer that is coupled to the plurality of control electronic devices of the second set and that receives the sensor signals from the second transmission channel and that provides control signals to selected control electronic devices to which the control de-multiplexer is coupled; and
a second ground wire that connects the sensor multiplexer and the control de-multiplexer.

3. The scanning system of claim 2 wherein the sensor de-multiplexer is secured to a first mobile carriage and the sensor multiplexer is secured to a second mobile carriage and wherein the means for driving a mobile carriage drives both the first and second mobile carriages.

4. The scanning system of claim 3 wherein movement of the first mobile carriage is synchronized with movement of the second mobile carriage.

5. The scanning system of claim 1 wherein the first transmission channel and the second transmission channel move through a take-up mechanism as the mobile carriage moves along the main scanning direction.

6. The scanning system of claim 1 wherein the sensor de-multiplexer and the sensor multiplexer are secured to the same mobile carriage.

7. The scanning system of claim 1 wherein the first transmission channel has a single wire.

8. An on-line scanning sensor system capable of detecting multiple characteristics of a traveling sheet of paper product as it progresses through or exits from a papermaking machine that comprises:
(a) a support member spanning across the traveling sheet of paper product;
(b) a mobile carriage, that is slidably attached to the support member, onto which a first set of sensor electronic devices is secured wherein, for at least a plurality of the sensor electronic devices, each has a sensor input;
(c) a first set of control electronic devices that is located remotely from the mobile carriage and which is separated by a distance of at least 50 meters from the mobile carriage, wherein for at least a plurality of the control electronic devices, each has a control output;
(d) a control multiplexer that is coupled to the plurality of control electronic devices and that receives input signals therefrom and that provides control signals of the plurality of control electronic devices for transmission through a first transmission channel that comprises a first wire;
(e) a sensor de-multiplexer that is coupled to the plurality of sensor electronic devices and that receives the control signals from the first transmission channel and that provides sensor signals to selected sensor electronic devices to which the sensor de-multiplexer is coupled;
a first ground wire that connects the control multiplexer and the sensor de-multiplexer; and
(f) means for driving a mobile carriage between a first end and a second end along a main scanning direction, which has a distance of at least six meters, such that the mobile carriage scans back and forth across at least a substantial portion of the paper product along a cross direction of the moving sheet, characterized in that the first set of sensor electronic devices is operated to detect a plurality of physical characteristics of the paper product.

9. The on-line scanning system of claim 8 further comprising:
a second set of sensor electronic devices, that is secured to a mobile carriage, wherein for at least a plurality of these sensor electronic devices, each has a sensor output;
a second set of control electronic devices, that is located remotely from any mobile carriage and which is separated by a distance of at least 50 meters from any mobile carriage, wherein for at least a plurality of these control electronic devices, each has a control input;
a sensor multiplexer that is coupled to the plurality of sensor electronic devices of the second set and that receives input signals therefrom and that provides sensor signals of the plurality of sensor electronic devices of the second set for transmission through a second transmission channel that comprises a second wire;
a control de-multiplexer that is coupled control outputs of the control electronic devices and that receives the sensor signals from the second transmission channel and that provides control signals to selected control electronic devices to which the control de-multiplexer is coupled; and
a second ground wire that connects the sensor multiplexer and the control de-multiplexer.

10. The on-line scanning system of claim 8 wherein first transmission channel and the second transmission channel moves through a take-up mechanism as the mobile carriage moves along the main scanning direction.

11. The on-line scanning system of claim 8 wherein the sensor de-multiplexer is secured to a first mobile carriage and the sensor multiplexer is secured to a second mobile carriage and wherein the means for driving a mobile carriage drives both the first and second mobile carriages.

12. The on-line scanning system of claim 11 wherein movement of the first mobile carriage is synchronized with movement of the second mobile carriage.

13. The on-line scanning system of claim 8 wherein the sensor de-multiplexer and sensor multiplexer are secured to the same mobile carriage.

14. The on-line scanning system of claim 8 wherein for the first set of electronic devices on the mobile carriage are configured to measure multiple physical parameters of the traveling sheet of paper.

15. The scanning system of claim 8 wherein the second transmission channel has a single wire.

16. A method for transmitting signals between sensor electronic devices and control electronic devices that comprise the steps of:
- securing a first set of sensor electronic devices to the mobile carriage wherein, for at least a plurality of the sensor electronic devices, each has a sensor input;
- providing a first set of control electronic devices that is located remotely from the mobile carriage and which is separated by a distance of at least 50 meters from the mobile carriage, wherein for at least a plurality of the control electronic devices, each has a control output;
- providing a control multiplexer that is coupled to the control electronic devices and that receives input signals therefrom and that provides control signals of the plurality of control electronic devices for transmission through a first transmission channel that comprises a first wire;
- providing a sensor de-multiplexer that is coupled to the sensor electronic devices and that receives the control signals from the first transmission channel and that provides sensor signals to selected sensor electronic devices to which the sensor de-multiplexer is coupled wherein the control multiplexer and the sensor de-multiplexer are connected to a first ground wire;
- moving the mobile carriage between a first end and a second end along a main scanning direction which has a distance of at least six meters; and
- operating the first set of sensor electronic devices and the first set of control electronic devices.

17. The method of claim 16 further comprising the steps of:
- providing a second set of sensor electronic devices, that is secured to a mobile carriage, wherein for at least a plurality of these sensor electronic devices, each has a sensor output;
- providing a second set of control electronic devices, that is located remotely from any mobile carriage and which is separated by a distance of at least 50 meters from any mobile carriage, wherein for at least a plurality of these control electronic devices, each has a control input;
- providing a sensor multiplexer that is coupled to the plurality of sensor electronic devices of the second set and that receives input signals therefrom and that provides sensor signals of the plurality of sensor electronic devices of the second set for transmission through a second transmission channel that comprises a second wire;
- providing a control de-multiplexer that is coupled to the control electronic devices of the second set and that receives the sensor signals from the second transmission channel and that provides control signals to selected control electronic devices to which the control de-multiplexer is coupled wherein the sensor multiplexer and the control de-multiplexer are connected to a second ground wire; and
- operating the second set of sensor electronic devices and the second set of control electronic devices.

18. The method of claim 16 wherein the sensor de-multiplexer is secured to a first mobile carriage and sensor multiplexer is secured to a second mobile carriage.

19. The method of claim 18 wherein movement of the first mobile carriage is synchronized with movement of the second mobile carriage.

20. The method of claim 17 wherein both the sensor de-multiplexer and sensor multiplexer are secured to the same mobile carriage.

* * * * *